United States Patent [19]

Kottirsch et al.

[11] Patent Number: 5,561,112
[45] Date of Patent: Oct. 1, 1996

[54] PSEUDOPEPTIDE ISOSTERES OF GLY-ASP AND THEIR USE AS ANTITHROMBIC AGENTS

[75] Inventors: Georg Kottirsch, Adelhausen-Rheinfelden; Rainer Metternich, Inzlingen, both of Germany

[73] Assignee: Sandoz Ltd., Basel, Switzerland

[21] Appl. No.: 204,836

[22] Filed: Mar. 1, 1994

Related U.S. Application Data

[63] Continuation of Ser. No. 28,454, Mar. 9, 1993, abandoned.

[30] Foreign Application Priority Data

Mar. 10, 1992 [DE] Germany .................. 42 07 544.0

[51] Int. Cl.⁶ .................................................. A61K 38/05
[52] U.S. Cl. .................. 514/19; 514/18; 530/331
[58] Field of Search ................. 514/18, 19; 530/331

[56] References Cited

U.S. PATENT DOCUMENTS

| | | | |
|---|---|---|---|
| 4,578,079 | 3/1986 | Ruoslahti et al. | 623/11 |
| 5,273,982 | 12/1993 | Alig | 514/315 |
| 5,354,738 | 10/1994 | Tjoeng | 514/19 |

FOREIGN PATENT DOCUMENTS

| | | |
|---|---|---|
| 0352249 | 1/1990 | European Pat. Off. . |
| 0372486A3 | 6/1990 | European Pat. Off. . |
| 0445796A3 | 9/1991 | European Pat. Off. . |

OTHER PUBLICATIONS

The Journal of Biological Chemistry vol. 268, No. 9, Issue of Mar. 25, 1993 pp. 6800–6808.
The Journal of Biological Chemistry vol. 268, No. 7, Issue of Mar. 5, 1993 pp. 4734–4741.
Thrombosis and Haemostasis 70 (3) 531–539 (1993).
Thrombosis and Haemostasis 70 (5) 838–847 (1993).
European Search Report.

*Primary Examiner*—Howard E. Schain
*Assistant Examiner*—David Lukton
*Attorney, Agent, or Firm*—Robert S. Honor; Melvyn M. Kassenoff; Thomas O. McGovern

[57] ABSTRACT

Pseudopeptides of formula I in free or salt form

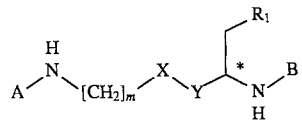

wherein A, B, $R_1$, X, Y and m are defined as in claim 1, and their use in the prophylactic and acute treatment of thrombosis.

10 Claims, No Drawings

PSEUDOPEPTIDE ISOSTERES OF GLY-ASP AND THEIR USE AS ANTITHROMBIC AGENTS

This is a continuation of patent application Ser. No 08/028,454, filed Mar. 9, 1993, now abandoned.

The invention relates to derivatives of β-amino acids which are isosteres of the dipeptide unit Gly-Asp. The compounds of the invention are pseudopeptides having anti-thrombotic activity. In particular the compounds are notable for the fact that they inhibit the binding of fibrinogen to the fibrinogen receptor on blood platelets (glycoprotein GP IIb/IIIa).

A decisive step in thrombus formation is the crosslinking of blood platelets by fibrinogen molecules. A requirement for this is activation of the platelets by agonists such as thrombin or adenosine diphosphate (ADP). This activation effects restructuring of the cell membrane, the consequence of which is that GPIIb/IIIa is exposed in active form.

GPIIb/IIIa belongs to the family of adhesion receptors known as integrins. Further ligands for GPIIb/IIIa, apart from fibrinogen, are fibronectin, vitronectin and the von Willebrand factor. These ligands play an important role in haemostatic processes, in that they bring about the adhesion and aggregation of platelets. Specific therapeutic inhibition of these interactions, may influence a decisive step in thrombus formation. The binding of fibrinogen, and of other ligands, is brought about by the peptide sequence Arg-Gly-Asp (RGD) (Ruoslahti E., Pierschbacher M., Cell 1986, 44, 517–18).

Fibrinogen possesses a further peptide sequence (His-His-Leu-Gly-Gly-Ala-Lys-Gln-Ala-Gly-Asp-Val) (SEQ ID NO. 1) on the C-terminus of the gamma chain with affinity for the fibrinogen receptor. Small synthetic peptides, which contain these sequences, may inhibit the binding of fibrinogen, fibronectin, vitronectin and the von Willebrand factor to GPIIb/IIIa, and may thus inhibit platelet aggregation (Plow et al. Proc. Natl. Acad. Sci. USA 1985, 82, 8057–61; Ruggeri et al. Proc. Natl. Acad. Sci. USA 1986, 5708–12; Ginsberg et al. J. Biol. Chem. 1985, 260, 3931–36; Gartner et al. J. Biol. Chem. 1987, 260, 11,891–94).

The present invention provides pseudopeptidic Arg-Gly-Asp analogues, in which the Gly-Asp unit is replaced by derivatives of β-amino acids, and in which Arg is replaced in most cases by a benzamidine-carboxylic acid. The new pseudopeptides inhibit platelet aggregation and thrombus formation.

Accordingly the present invention relates to pseudopeptides of formula I in free or in salt form

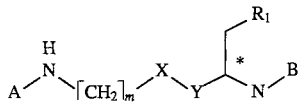

wherein
$R_1$ is a group of formula —COOH, —COOM or —COO($C_1$–$C_4$)alkyl, preferably COOH
wherein
is an alkali or alkaline earth metal atom, preferably Li
is —$CH_2$—, —CH=, —CO—, —C*HOH— or —C*HO(($C_1$–$C_4$)alkyl)-, preferably —$CH_2$—, or preferably also X and $R_1$ together are a

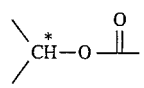

group
Y is —$(CH_2)_m$—, =CH— or —NH—, preferably —$(CH_2)_m$— and
m is 1 or 2, preferably 2
A is either a group of formula

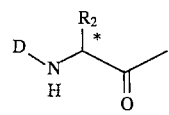

wherein
D is hydrogen, a protecting group Z or an α-amino acid which is bonded via its carbonyl group,
$R_2$ is a group of formula

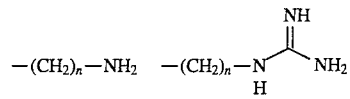

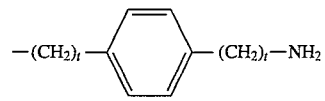

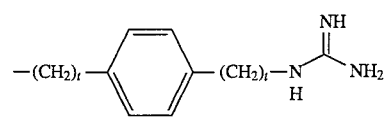

or

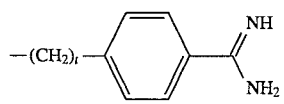

wherein
n is 3 or 4 and
t is 0 or 1
or
A is a group of formula

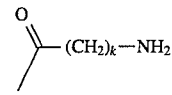

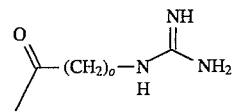

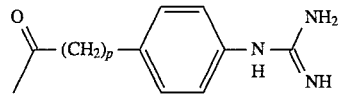

or preferably

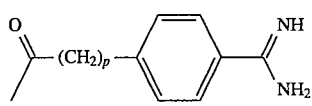

wherein
k is 3, 4, 5 or 6,
o is 3, 4 or 5, and
p is 0, 1 or 2, preferably 1
B is either a group of formula

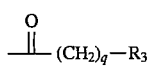

wherein
q is 1 or 2, preferbly 1 and
$R_3$ is $(C_1–C_4)$alkyl, $(CH_3)_2CH—$, tert.-butyl, 1-adamantyl, trimethylsilyl, 1-naphthyl, phenyl, 3-indolyl or $(C_1–C_4)$-alkoxyphenyl, preferably $(CH_3)_2CH$, $(C_1–C_4)$-alkoxyphenyl (e.g. p methoxyphenyl), or 1-adamantyl, epecially $(CH_3)_2CH$, or
B is a group of formula

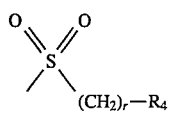

wherein
r is 0, 1 or 2, preferably 0
and
$R_4$ is $(C_1–C_4)$alkyl, 2-propyl, tert.-butyl, phenyl, p-$(C_1–C_4)$alkoxyphenyl, 1-naphthyl, tolyl, mesyl or trisyl, preferably mesyl or
B is a group of formula

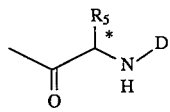

wherein
D is hydrogen or a protecting group Z
and
$R_5$ is phenyl-$(CH_2)_t$—,
   indol-3-yl-$(CH_2)_t$—,
   naphth-1-yl-$(CH_2)_t$—,
   adamant-1-yl-$(CH_2)_t$—,
   prop-2-yl-$(CH_2)_t$—,
   trimethylsilyl-$(CH_2)_t$— or
   tert.-butyl-$(CH_2)_t$—, wherein t is defined as above,
or
B is an α-amino acid that is bonded via its carbonyl group.
   Each asymmetrical C-atom indicated by an asterisk (*) in the formulae may be of either R or S configuration.
   In the formulae, $(C_1–C_4)$alkyl is preferably methyl, and $(C_1–C_4)$alkoxy is preferably methoxy. The protecting group Z is preferably a benzyloxycarbonyl or tert.-butyloxycarbonyl group. Where D and/or B denote an α-amino acid, this may be a naturally occurring α-amino acid, or an unnatural α-amino acid.
   In the present description unless otherwise indicated terms such as "compounds of formula I" embrace the compounds in salt form as well as in free form.

Preferred compounds are those of formula I'

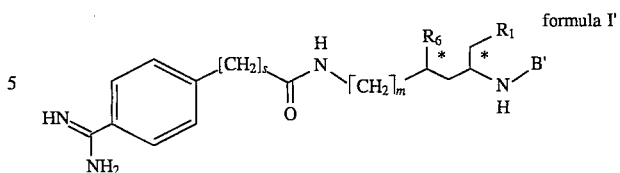

wherein
$R_1$ and m are defined as above, s is 0 and 1, $R_6$=H, OH or O$(C_1–C_4)$alkyl, or
$R_1$ and $R_6$ together form a —O—CO— group
B' is either a group of formula

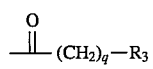

wherein $R_3$ and q are defined as above, or B' is a group of formula

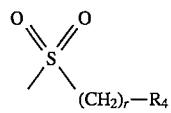

wherein $R_4$ and r are defined as above, or B' is a group of formula

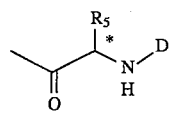

wherein $R_5$ and D are defined as above.
   Especially preferred compounds are those having formula I"

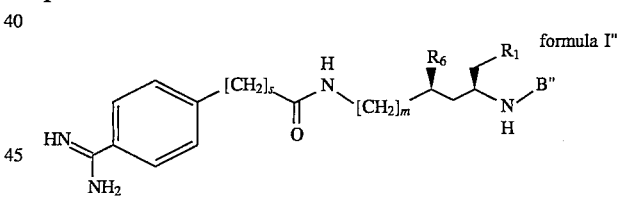

wherein $R_1$, $R_6$, m and s are defined as above, or $R_1$ and $R_6$ together form a —O—CO— group and B" is a group of formula

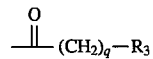

wherein q and $R_3$ are defined as above,
   The most preferred compounds of formula I are those of the following formulae II, III, IV, V, VI, VII:

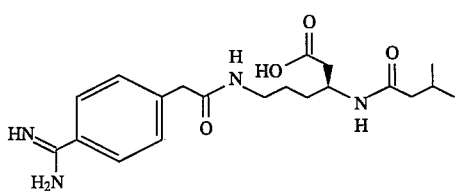

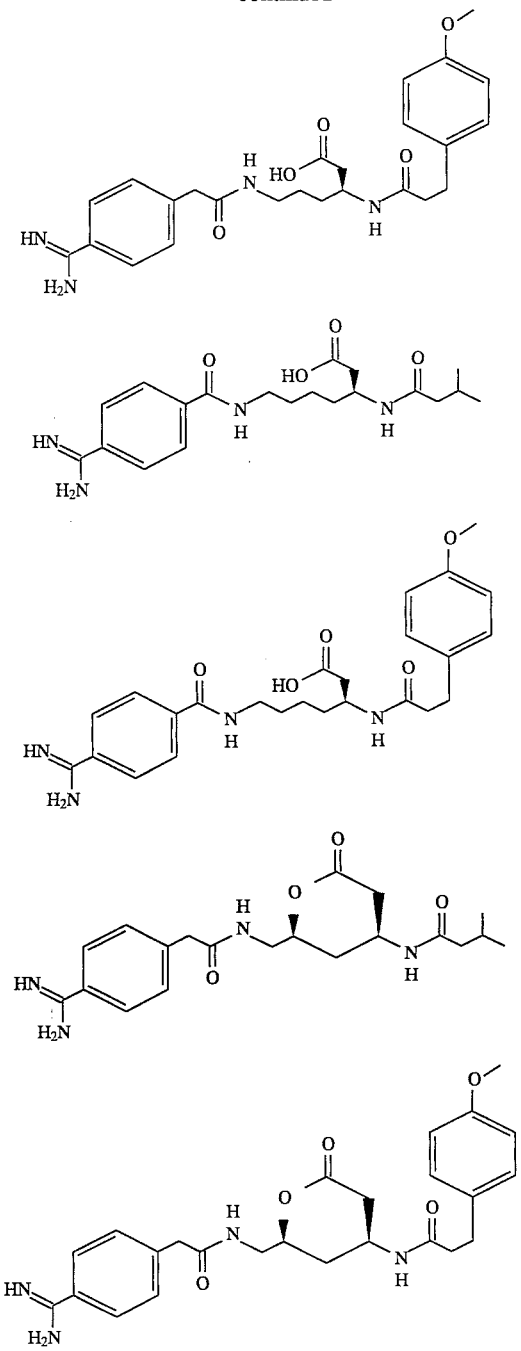

These are the compounds of examples 2, 3, 6, 9, 8 and 7 respectively. The compounds of formula I of the type which includes the compounds of formulae II to V above may be synthesized using procedures analogous to the following synthesis scheme 1.

Synthesis scheme 1:

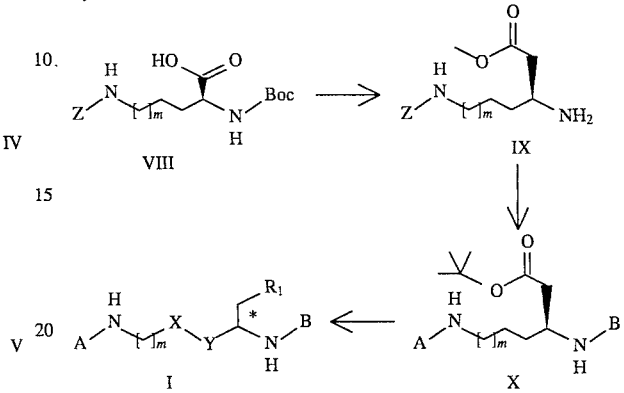

In the above formulae, $[v]_m$— is the group $[CH_2]_m$, and m, A, B, X, Y and $R_1$ are as defined above.

In accordance with synthesis scheme 1, compounds of formula I with $X=Y=CH_2$, $R_1=COOH$ and m=1 or 2, are produced from compound X by treatment with trifluoroacetic acid at room temperature. Compound X is obtained from the z protected ester IX, by coupling the amino group with iso-valeric acid or p-methoxyphenylpropanoic acid (depending on radical B) whilst adding DCC and HOBT, then hydrolyzing the methylester with LiOH, converting the acid into the tert.-butylester by means of tert.-butyl-2,2,2-trichloroacetimidate, removing the protecting group Z under reducing conditions with $H_2$/Pd-C, followed by coupling with an appropriate radical A [e.g. A signifies (p-amidinophenyl)-$(CH_2)_s$-COOH wherein s is as defined above] again adding DCC and HOBT. The methylester IX is obtained from the Z=Boc protected amino acid VIII by chain lengthening of the carboxylic acid using the diazomethane/$Ag_2O$ method (Helv. Chim. Act. 58, 969 (1975)) and removing the Boc group with trifluoroacetic acid at room temperature.

Furthermore, compounds of formula I of the type which includes the compounds of formulae VI and VII above may be produced using procedures analogous to the following synthesis scheme 2.

Synthesis scheme 2:

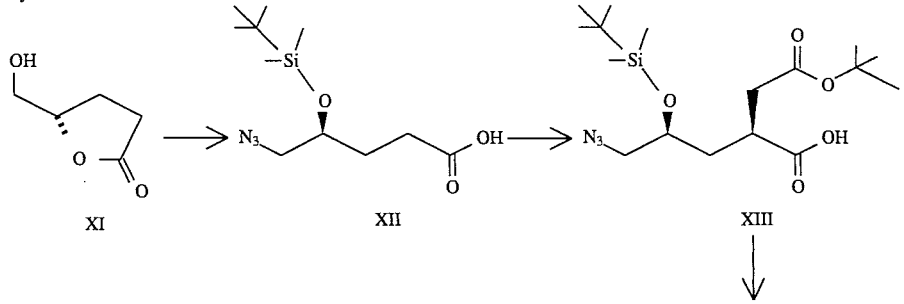

Synthesis scheme 2:

-continued

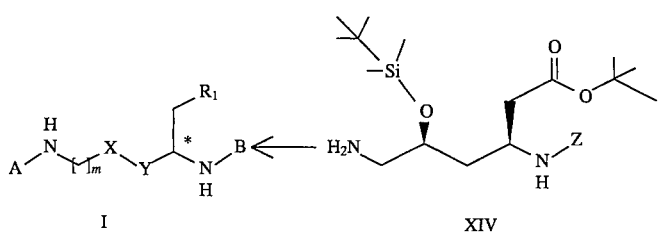

In the above formulae, $[v]_m$ is $[CH_2]_m$, and m, A, B, X, Y and $R_1$ are as defined above.

In accordance with synthesis scheme 2, compounds of formula I, wherein m is 1, X and $R_1$ together form a HC*—O—CO— group and Y is a $CH_2$— group, may be produced from compound XIV by coupling with an appropriate radical A (analogously to synthesis scheme 1), removing the protecting group under reducing conditions with $H_2$/Pd-C, followed by coupling with an appropriate radical B (analogously to synthesis scheme 1) and subsequently removing the protecting groups with trifluoroacetic acid at room temperature. Compound XIV is obtained from compound XIII by converting the carboxylic acid into a Z-protected amine with diphenylphosphorylazide and triethylamine in the presence of benzyl alcohol, and reducing the azido group with triphenylphosphine in tetrahydrofuran. The carboxylic acid XIII is obtained from compound XII by means of enantio-selective introduction of the acid side chain in 3 stages: a) coupling with the Evans oxazolidinone to introduce a chiral auxiliary group (J. Am. Chem. Soc. 1990, 112, 4011); b) formation of the amide-enolate with Li-hexamethyldisilazide and reaction with bromoacetic acid tert.-butylester; c) removal of the chiral auxiliary group with Li-perhydroxide. The azidocarboxylic acid XII is obtained from the lactone XI, by mesylation of the alcohol with methanesulphonyl chloride, azidation with sodium azide, opening the lactone with caustic soda solution in ethanol and reacting with tert.-butyldimethylsilyl chloride in the presence of imidazole to introduce the alcohol protecting group.

The compounds of formula I inhibit the binding of fibrinogen to the fibrinogen receptor blood platelets (glycoprotein GP IIb/IIIa). As a result of this property, the compounds prevent the aggregation of human blood platelets and the formation of clots, and may accordingly be used to prevent and treat thrombosis, apoplexy, cardiac infarction, inflammation, arterial sclerosis and tumours. Further therapeutic fields of use are: osteoporosis, acute reocclusion following PTCA and addition during thrombolysis.

The abbreviations used in the description and in the following examples have the following significances.

Z=benzoyloxycarbonyl
BOC=tert.-butyloxycarbonyl
DCC=dicyclohexylcarbodiimide
HOBT=hydroxybenzotriazole
DMF=dimethylformamide
THF=tetrahydrofuran
TFA=trifluoroacetic acid
EtOAc=ethyl acetate
RP=reversed phase
Pd/C (10% )=palladium-charcoal catalyst containing 10% palladium
LiOH=lithium hydroxide
PTCA=percutaneous luminal coronary angioplasty
TBDMS=tert.-butyl-dimethylsilyl-chlorosilane
MeOH=methanol
LiHMDS=lithium hexamethyl disilazide
DPPA=diphenylphosphoryl azide
EtOH=ethanol
NMM=N-methylmorpholine

EXAMPLE 1

(S)-3-(N-tosylamino)-6-[N-(p-amidinophenylacetyl)amino] hexanoic acid

A) (S)-3-amino-6-[N-(benzyloxycarbonyl)amino]hexanoic acid methylester trifluoroacetate.

0.69 ml of chloroformic acid isobutyl ester are added in dropwise to a solution of 1.95 g of Boc-Orn(Z)-OH and 0.74 ml of $NEt_3$ in 12 ml of THF at −15° C. After 30 minutes at −15° C., the precipitated hydrochloride is filtered off and the filtrate is mixed at −15° C. with 40 ml (8 mmol) of an ethereal solution of diazomethane. The reaction mixture is stirred for 4 hours at 0° C., and left to stand for a further 16 hours at 4° C. Water is added, and the solution is extracted with ether. The ether phase is washed with saturated aqueous bicarbonate solution, dried over sodium sulphate and concentrated by evaporation. The residue obtained is taken up in 15 ml of methanol, mixed with 246 mg of silver(I) oxide and heated under reflux for 12 hours. The solid material is removed by filtration, the methanol evaporated off and the residue chromatographed on silica gel (ethyl acetate/hexane 1:1). The product thus isolated is (S)-3-N-Boc-amino-6-N-Z-aminohexanoic acid methylester. MS: 395 (M+H)+.

The product obtained is mixed at 0° C. with 10 ml of methylene chloride and 10 ml of trifluoroacetic acid, stirred for 1 hour at room temperature, the solvent is removed by vacuum distillation, and the residue is dried for 24 hours in a high vacuum. The (S)-3-amino-6-[N-(benzyloxycarbonyl)amino]hexanoic acid methylester trifluoroacetate product is obtained as a colourless solid.

B) (S)-3-N-tosylamino-6-N-Z-aminohexanoic acid methylester 1.3 g of the trifluoroacetate from stage A is dissolved in 5 ml of DMF together with 0.75 ml of triethylamine, and then 468 mg of tosyl chloride is added. After 2 hours, water is added and extraction with ether carried out. The ether phase is washed with water, dried over sodium sulphate, the ether is evaporated off and the residue chromatographed on silica gel (ethyl acetate/hexane 1:1). The thus isolated product is (S)-3-N-tosylamino-6-N-Z-aminohexanoic acid methylester; MS: 449 (M+H)+.

C) (S)-3-(N-tosylamino)-6-[N-(p-amidinophenylacetyl)amino]hexanoic acid.

The product obtained according to stage B) is dissolved in 20 ml of methanol and hydrogenated in the presence of 0.3 g of Pd/C (10%) and 1.34 ml of 1N hydrochloric acid. When the reaction has ended, the catalyst is removed by filtration, the methanol is evaporated off and the residue is dried under high vacuum. 500 mg of (S)-3-(N-tosylamino)-6-aminohexanoic acid methylester hydrochloride is obtained as a colourless foam. 0.5 g of the hydrochloride, 373 mg of N-Boc-p-amidinophenylacetic acid (produced by the Bocylation of p-amidinophenylacetic acid (Pharmazie 29, 256–262)), 0.19 ml of triethylamine and 199 mg of HOBT are dissolved in 10 ml of DMF and mixed with 276 mg of DCC. After 16 hours at room temperature, the precipitated solid is removed by filtration, the DMF is evaporated off and the residue is taken up in ethyl acetate. The ethyl acetate phase is washed with water, dried over sodium sulphate, concentrated by evaporation, and the residue chromatographed on silica gel (ethyl acetate). The product obtained is mixed with a solution of 0.2 ml of anisole in 5 ml of TFA, stirred for 2 hours at room temperature and added dropwise to 300 ml of ether. The precipitated solid is filtered off, dissolved in a mixture of 2 ml of methanol and 1 ml of water, and mixed with 57 mg of LiOH-H$_2$O. After 5 hours at room temperature, the methanol is evaporated off and the aqueous solution is neutralized with 0.13 ml of TFA. The precipitated solid is filtered off, dried and recrystallized from methanol/ether. The (S)-3-(N-tosylamino)-6-[N-(p-amidinophenylacetyl)amino]hexanioc acid trifluoroacetate product is obtained as a white solid, MS: 461 (M+H)+. The free compound is obtained from the trifluoroacetate in known manner.

EXAMPLE 2

(S)-3-[N-(3-methylbutyryl)amino]-6-[N-(p-amidinophenylacetyl)amino]hexanoic acid A) (S)-3-[N-(3-methylbutyryl)amino]-6-N-Z-aminohexanoic acid methylester 1.3 g of the trifluoroacetate from stage A of example 1, 250 mg of isovaleric acid, 0.34 ml of triethylamine and 363 mg of HOBT are dissolved in 5 ml of DMF and mixed with 505 mg of DCC. After 16 hours, the precipitated deposit is removed by filtration, the DMF is evaporated off and the residue is dissolved in ethyl acetate. The ethyl acetate phase is washed with saturated aqueous bicarbonate solution and water, dried over sodium sulphate, and the solvent is removed under vacuum. The residue is purified by recrystallization from ethyl acetate/ether, and the (S)-3-[N3-methylbutyryl)amino]-6-N-Z-aminohexanoic acid methylester product is obtained as colourless crystals. MS: 379 (M+H)+.

B) (S)-3-[N-(3-methylbutyryl)amino]-6-[N-(p-amidinophenylacetyl)-amino]hexanoic acid.

560 mg of the product of stage A) of example 2 is dissolved in 20 ml of methanol and hydrogenated in the presence of 0.3 g of Pd/C (10%) and 1.41 ml of 1N hydrochloric acid. After working up as described in stage C) of example 1, (S)-3-[N-(3-methylbutyryl)amino]-6-aminohexanoic acid methylester hydrochloride is obtained in the form of a colourless oil. 400 mg of the hydrochloride and 392 mg of N-Boc-p-amidinophenylacetic acid, together with 0.2 ml of triethylamine, 259 mg of HOBT and 290 mg of DCC, are reacted and worked up as described in stage C) of example 1. After cleavage of the Boc group with TFA and hydrolysis of the methylester with LiOH-H$_2$O analogously to stage C) of example 1, the crude product obtained is recrystallized from methanol. The (S)-3-[N-(3-methylbutyryl)amino]-6-[N-(p-amidinophenylacetyl)amino]hexanoic acid trifluoroacetate product is isolated as a white powder; MS: 391 (M+H)+. The free compound is obtained from the trifluoroacetate in known manner.

EXAMPLE 3

(S)-3-N-[3-(p-methoxyphenyl)propionyl]amino-6-[N-(p-amidinophenylacetyl)amino]hexanoic acid A) (S)-3-N-[3-(p-methoxyphenyl)propionyl]amino-6-N-Z-aminohexanoic acid methylester.

0.7 g of the trifluoroacetate from stage A) of example 1 and 256 mg of 3-(p-methoxy)propionic acid, together with 0.21 ml of triethylamine, 256 mg of HOBT and 313 mg of DCC, are reacted and worked up as described in stage A) of example 2. The crude product is recrystallized from ether. The (S)-3-N-[3-(p-methoxyphenyl)propionyl]amino-6-N-Z-aminohexanoic acid methylester product is obtained in the form of white crystals; MS: 457 (M+H)+.

B) (S)-3-N-[3-(p-methoxyphenyl)propionyl]amino-6-[N-(p-amidinophenylacetyl)amino]hexanoic acid 440 mg of the methylester from stage B) of example 3 is hydrogenated analogously to stage C) of example 1, and the hydrochloride obtained is reacted and worked up with 164 mg of N-Boc-p-amidinophenylacetic acid, 0.13 ml of triethylamine, 164 mg of HOBT and 200 mg of DCC, as described in stage C) of example 1. The product is deprotected with TFA and LiOH-H$_2$O analogously to stage C) of example 1, and the crude product is recrystallized from methanol/water. The (S)-3-N-[3-(p-methoxyphenyl)propionyl]amino-6-[N-(p-amidinophenylacetyl)-amino]hexanoic acid trifluoroacetate product is obtained as a white powder. MS: 583 (M+H)+. The free compound is produced from the trifluoroacetate in known manner.

EXAMPLE 4

(S)-3-[N-(adamant-1-ylacetyl)amino]-6-[N-(p-amidinophenylacetyl) amino]hexanoic acid A) (S)-3-[N-(adamant-1-ylacetyl)amino]-6-N-Z-aminohexanoic acid methylester 0.7 g of the trifluoroacetate from stage A) of example 1 is reacted and worked up with 246 mg of adamant-1-ylacetic acid, 0.21 ml of triethylamine, 246 mg of HOBT and 331 mg of DCC, as described in stage A of example 2. The crude product is chromatographed on silica gel (ethyl acetate), and the (S)-3-[N-(adamant-1-ylacetyl)amino]-6-N-Z-aminohexanoic acid methylester product is isolated as a colourless oil; MS: 471 (M+H)+.

B) (S)-3-[N-(adamant-1-ylacetyl)amino-6-N-Z-aminohexanoic acid tert.butylester 460 mg of the methylester from stage A) of example 4 is dissolved in 4 ml of MeOH and 2 ml of water, and mixed with 84 mg of LiOH-H$_2$O. After 4 hours at room temperature, the mixture is neutralized with 1N hydrochloric acid and extracted with ethyl acetate. The ethyl acetate phase is dried over sodium sulphate, and the solvent removed under vacuum. 400 mg of crude product are obtained, which is dissolved in 2 ml of THF and mixed with a solution of 479 mg of tert.-butyl-2,2,2-trichloroacetimidate in 2.5 ml of cyclohexane. After adding 0.069 ml of boron trifluoroetherate, the mixture is stirred for 3 hours at room temperature. The reaction mixture is mixed with 5% aqueous bicarbonate solution, extracted with ethyl acetate, the ethyl acetate phase is washed with saturated aqueous sodium chloride solution, dried over sodium sulphate and the solvent concentrated by evaporation. The residue is taken up in methylene chloride/hexane 1/1, the insoluble trichloroacetamide filtered off and the solvent evaporated off. The crude oil obtained is chromatographed on silica gel (ethyl acetate/hexane 1/1), to give the (S)-3-[N-(adamant-1-ylacetyl)amino]-6-N-Z-aminohexanoic acid tert.butylester product as a colourless oil. MS: 513 (M+H)+.

C) (S)-3-[N-(adamant-1-ylacetyl)amino]-6-[N-(p-amidinophenylacetyl)amino]hexanoic acid 225 mg of the tert.-butylester from stage B) of example 4 is dissolved in 20 ml of ethanol, and hydrogenated in the presence of 0.1 g of Pd/C (10%) and 0.028 ml of acetic acid, as described in stage C) of example 1. The crude product obtained is dissolved in 5 ml of DMF, and reacted with 119 mg of N-Boc-p-amidinophenylacetic acid, 0.061 ml of triethylamine, 73 mg of HOBT and 90 mg of DCC, analogously to stage C) of example 1. The crude product obtained after the work up is chromatographed on silica gel (ethyl acetate) and the pure product is mixed with a solution of 5 ml of TFA in 0.2 ml of anisole.

After 3 hours at room temperature, the reaction mixture is added dropwise to 300 ml of ether, and the precipitated solid is filtered off. After drying in a high vacuum, the (S)-3-[N-(adamant- 1-ylacetyl)amino]-6-[N-(p-amidinophenylacetyl)amino]hexanoic acid trifluoroacetate product is obtained as white powder; MS: 505 (M+H)+.

The free compound is produced from the trifluoroacetate in known manner.

EXAMPLE 5

(S)-3-[N-(3-adamant-1-ylpropionyl)amino]-6-[N-(p-amidinophenylacetyl)amino]hexanoic acid A) (S)-3-[N-(3-adamant-1-ylpropionyl)amino]-6-N-Z-amino-hexanoic acid methylester (S)-3-[N-(3-adamant- 1-ylpropionyl)amino]-6-N-Z-amino-hexanoic acid methylester is obtained by reacting 0.85 g of the trifluoroacetate of stage A) of example 1, with 423 mg of 3-adamant-ylpropionic acid, 0.28 ml of triethylamine, 337 mg of HOBT and 418 mg of DCC, followed by purification by chromatography (silica gel, ethyl acetate), analogously to stage A) of example 2; MS: 485 (M+H)+.

(S)-3-[N-(3-adamant-1-ylpropionyl)amino]-6-N-Z-aminohexanoic acid tert.-butylester The 500 mg of methylester from stage A) of example 5 is hydrolyzed as described in stage B of example 4 with 173 mg of LiOH-H$_2$O, and reacted with 575 mg of tert.-butyl-2,2,2-trichloroacetimidate and 0.06 ml of boron trifluoroetherate. After working up as described in stage B of example 1, the (S)-3-[N-(3-adamant-1-ylpropionyl)amino]-6-N-Z-aminohexanoic acid tert.-butylester product is isolated; MS: 527 (M+H)+.

C) (S)-3-[N-(3-adamant-1-ylpropionyl)amino]-6-[N-(p-amidinophenylacetyl)amino]hexanoic acid 510 mg of the product from stage B) of example 5 is hydrogenated analogously to stage C) of example 4, coupled with 430 mg of N-Boc-p-amidinophenylacetic acid, and after purification by chromatography (silica gel/ethyl acetate) the product obtained is deprotected with 5 ml of TFA/anisole (95/5). Following precipitation from ether, (S)-3-[N-(3-adamant- 1-ylpropionyl)amino]-6-[N-(p-amidinophenylacetyl)amino]hexanoic acid trifluoroacetate is obtained as a white powder, analogously to stage C) of example 5; MS 497 (M+H)+. The free compound is produced from the trifluoroacetate in known manner.

EXAMPLE 6

(S)-3-(N-(3-methylbutyryl)amino]-7-[N-(p-amidinobenzoyl)amino]heptanoic acid

A) (S)-3-amino-6-N-Z-aminoheptanoic acid methylester 4.04 g of Boc-Lys(Z)-OH, 1.38 ml of chloroformic acid isobutylester, 1.44 ml of triethylamine and 80 ml (16 mmol) of ethereal diazomethane solution are reacted together, then further reacted with 490 mg of silver(I) oxide and worked up, analogously to stage A) of example 1, then the crude product is purified by chromatography (silica gel, ethyl acetate/hexane 1/1) to produce (S)-3-N-Boc-amino-6-N-Z-aminoheptanoic acid methylester. MS: 409 (M+H)+. The methylester is dissolved in 15 ml of methylene chloride and mixed with 15 ml of TFA. After 1 hour, the TFA and the solvent are removed under vacuum and the residue is dried under high vacuum, to yield the (S)-3-amino-6-N-Z-aminoheptanoic acid methylester trifluoroacetate product.

B) (S)-3-[N-(3-methylbutyryl)amino]-7-N-Z-aminoheptanoic acid methylester 4.1 g of the trifluoroacetate from stage A) of example 6 is reacted with 1.0 g of isovaleric acid, 1.36 ml of triethylamine, 1.65 g of HOBT and 2.02 g of DCC as described in stage A) of example 2, and worked up analogously. The crude product obtained is recrystallized from ether, to yield the (S)-3-[N-(3-methylbutyryl)amino]-7-N-Z-aminoheptanoic acid methylester product; MS: 393 (M+H)+.

C) (S)-3-[N-(3-methytbutyryl)amino]-7-N-Z-aminoheptanoic acid tert.butylester

As described in stage B) of example 4, 3.25 g of methylester from stage B) of example 6 are saponified with 1.36 g of LiOH-H$_2$O and reacted with 4.04 g of tert.-butyl-2,2,2-trichloroacetimidate and 0.42 ml of boron trifluoroetherate, to yield the (S)-3-[N-(3-methylbutyryl)amino]-7-N-Z-aminoheptanoic acid tert.-butylester product; MS: 435 (M+H)+.

D) (S)-3-[N-(3-methylbutyryl)amino-7-[N-(p-amidinobenzoyl)amino]heptanoic acid

After hydrogenation of 2.2 g of the product from stage C) of example 6 analogously to stage C) of example 4, the product is further reacted with 1.34 g of N-Boc-p-amidinobenzoic acid (preparation analogously to N-Boc-p-amidinophenylacetic acid), 0.7 ml of triethylamine, 0.852 g of HOBT and 1.04 g of DCC, as in stage C) of example 4, and subsequently deprotected with 25 ml of TFA/anisole (95/5), and worked up, to produce the (S)-3-[N-(3-methylbutyryl)amino]-7-[N-(p-amidinobenzoyl)amino]heptanoic acid trifluoroacetate product in the form of a white powder; MS: 391 (M+H)+. The free compound is produced from the trifluoroacetate in known manner.

EXAMPLE 7

(3S,5S)-6-(4-amidinophenylacetylamino)-5-hydroxy-3-(4-methoxyphenylpropionylamino)-hexanoic acid-δ-lactone A) (4S)-4-hydroxy-5-O-mesyl-valeric acid-γ-lactone (4S)-4,5-dihydroxy-valeric acid-γ-lactone (16.3 g, 140 mmol) and triethylamine (21.52 ml, 154 mmol) are dissolved in methylene chloride and the solution cooled to −30° C. Methanesulphonyl chloride (12.0 ml, 154 mmol) is then added dropwise whilst stirring. The solution is then stirred for 15 minutes at −30° C. and heated to 18° C. over the course of 1½ hours. The suspension obtained is added to 0.5N HCl and extracted several times with ether. The combined organic phases are washed with saturated aqueous NaHCO$_3$ solution and saturated aqueous NaCl solution. After drying over Na$_2$SO$_4$ and concentrating on a rotary evaporator, the (4S)-4-hydroxy-5-O-mesyl-valeric acid-γ-lactone product is obtained as an oil, which is used immediately in the next reaction step.

B) (4S)-4-hydroxy-5-azido-valeric acid-γ-lactone

The mesylate from stage A) of example 7 (25.0 g, 128.7 mmol) is dissolved in DMSO, the solution mixed at room temperature with sodium azide (16.74 g, 257.4 mmol), and stirred for 1½ hours at 100° C. The brown suspension is cooled and the DMSO is distilled off under vacuum. The residue is taken up in EtOAc, filtered over Hyflo and concentrated under vacuum. Vacuum distillation (0.16 mbar) yields the title compound as a colourless oil, $\alpha_D$=+79.9° (c=2.2 in CHCl$_3$).

C) (4S)-5-azido-4-[((1,1-dimethylethyl)-dimethylsilyl)oxy]pentanoic acid (4S)-4-hydroxy-5-azido-valeric acid-γ-lactone (12.28 g, 87.01 mmol) from stage B) of example 7 is dissolved in 435 ml of ethanol, and then 43.5 ml of 2N aqueous NaOH are added whilst stirring at room temperature. After standing for ½ hour at room temperature, the solution is concentrated on a rotary evaporator and dried in a high vacuum. The residue obtained (16.94 g) is mixed with 174 ml of DMF, imidazole (29.63 g, 435.05 mmol) and TBDMS-Cl (48.3 g, 313.24 mmol), and stirred for 19 hours at room temperature. The suspension obtained is added to ice/1N aqueous NaHSO$_4$ solution, and extracted several times with ether. The combined organic phases are dried over Na$_2$SO$_4$ and concentrated in a vacuum. The residue is dissolved in 435 ml of methanol, and mixed with 18.44 g of Na$_2$CO$_3$ (in 87.0 ml H$_2$O) whilst stirring at room temperature, then agitated for ½ hour at room temperature. The suspension obtained is mixed with 435 ml of H$_2$O and extracted twice with hexane. The combined hexane phases are washed with methanol/H$_2$O (1:1), and the combined aqueous phases are acidified with NaHSO$_4$. After extraction with hexane and washing with saturated aqueous NaCl solution, the organic phase is dried over Na$_2$SO$_4$ and concentrated on a rotary evaporator. After thin-layer chromatography and $^1$H-NMR, the crude (4S)-5-azido-4-[((1,1-dimethylethyl)dimethylsilyl)oxy]-pentanoic acid product obtained is practically pure and is further employed without further purification. MS: 274 (M+H)+.

D) (3(4S),4R)-3-[5-azido-4-(((1,1-dimethylethyl)dimethylsilyl)-oxy)-1-oxopentyl]-4-(phenylmethyl)-2-oxazolidinone.

The optically active pentanoic acid derivative from stage C) of example 7 (19.79 g, 72.37 mmols) is dissolved in 405 ml of dry THF, cooled to −78° C., mixed with 13.5 ml of triethylamine (97 mmol) and then with 10.4 ml (84.7 mmol) of pivaloyl chloride. After 5 minutes at −78° C., the mixture is warmed over the course of 1 hour to 0° C., and cooled again to −78° C. In a second reaction container, (4R)-4-phenylmethyl-2-oxazolidonone (15.65 g, 88.3 mmol) is dissolved in 405 ml of anhydrous THF, cooled to −78° C., mixed with n-butyllithium (56.1 ml of 1.6M solution), and agitated for 0.25 hours at −78° C. The azaenolate thus produced is mixed at −78° C. using a pressure needle with the mixed acid anhydride which is previously prepared in situ. The cooling bath is removed and stirring is effected for 1 hour. The reaction mixture is added to ice/NaHSO$_4$ solution, extracted with EtOAc, the organic phases are washed with saturated aqueous NaHCO$_3$ solution and saturated aqueous NaCl solution, and subsequently dried over Na$_2$SO$_4$ and concentrated in a vacuum. The crude material obtained is chromatographed over silica gel (hexane/EtOAc, 3:1). The title compound is obtained as a white solid; MS: 433 (M+H)+.

E) (3(2S,4S),4R)-3-[5-azido-4-(((1,1-dimethylethyl)dimethyl-silyl)-oxy)- 2-tert.-butyloxy-carbonylmethyl-1-oxopentyl]-4-(phenylmethyl)-2-oxazolidinone The optically pure imide from stage D) of example 7 (19.05 g, 44 mmol) is dissolved in 44 mmol of THF, and added to a solution, cooled to −78° C., of LiHMDS (48.4 ml of 1.0M solution) in 66 ml of THF. After ½ hour at −78° C., bromoacetic acid-tert.-butylester (9.7 ml, 66 mmol) is added dropwise over the course of 20 minutes to the enolate which is cooled to −78° C. After standing for 1 hour at −78° C., the mixture is heated to 0° C. and then saturated aqueous NH$_4$Cl solution is added to the reaction mixture. After extraction with ether, the combined organic phases are washed with saturated aqueous NaHCO$_3$ solution and saturated aqueous NaCl solution, dried over Na$_2$SO$_4$ and concentrated in a vacuum. According to $^1$H-NMR, the product exists as a diastereoisomeric mixture (90:10) of (3(2S,4S),4R):(3(2R,4S),4R). After chromatography over silica gel (hexane/EtOAc, 6:1), the title compound is obtained in pure diastereoisomeric form as a colourless oil; MS: 521 (M-N$_2$+3H)+

F) (3S,5S)-6-azido-5-[((1,1-dimethylethyl)-dimethylsilyl)oxy]- 3-hydroxycarbonyl-hexanoic acid-tert.-butylester.

The title compound from stage E) of example 7 (21.5 g, 39.4 mmol) is dissolved in 500 ml of THF, mixed in succession with 180 ml of H$_2$O, 16.7 ml of H$_2$O$_2$ (30% solution) and LiOH (3.3 g, 78.8 mmol), and agitated for 1½ hours at 0° C. Then, Na$_2$SO$_3$ (17.1 g, 136 mmol) in 120 ml of H$_2$O is added, and stirring is effected for 5 minutes at 0° C. The reaction mixture is acidified with 1N aqueous NaHSO$_4$ solution, and extracted several times with ether. The combined organic phases are washed with saturated aqueous NaCl solution, dried over Na$_2$SO$_4$ and concentrated under vacuum. The crude product obtained is taken up in hexane. The resulting (4R)-4-phenylmethyl-2-oxazolidinone is filtered off and the hexanoic acid tert.-butylester derivative is obtained in pure form by concentrating the filtrate and drying it under high vacuum. MS: 410 (M+H)+ from the Na salt.

G) (3S,5S)-6-azido-5-[((1,1-dimethylethyl)-dimethylsilyl)oxy]- 3-benzyloxycarbonylamino-hexanoic acid tert.-butylester The title compound from stage F) of example 7 (1.55 g, 4.0 mmol) is dissolved in 20 ml of anhydrous toluene, and mixed in succession with DPPA (956 μl (95%), 4.2 mmol) and triethylamine (613 μl, 4.4 mmol), and stirred under reflux for ½ hour. After cooling to ca. 40° C., benzyl alcohol (4.14 ml, 40 mmol) is added and the mixture stirred under reflux for a further 60 minutes. The reaction solution is cooled to room temperature, mixed with additional toluene, washed with saturated aqueous NaHCO$_3$ solution, 10% tartaric acid solution and saturated aqueous NaCl solution, dried over Na$_2$SO$_4$ and concentrated under vacuum. The crude product is chromatographed on silica gel (hexane/EtOAc, 6:1), and the title compound is obtained in pure form; MS: 493 (M+H)+.

H) (3S,5S)-6-[4-(tert.-butyloxycarbonyl)amidino-phenylacetylamino]-5-[((1,1-dimethylethyl)dimethylsilyl)oxy]- 3-benzyloxycarbonylamino-hexanoic acid tert.-butylester The title compound from stage G) of example 7 (1.18 g, 2.4 mmol) is dissolved in THF (12.0 ml) and is reacted with triphenylphosphine (0.66 g, 2.52 mmol) analogously to a procedure described in the literature (Tetrahedron Lett. 24, 763 (1983) initially at room temperature (17 hours) and then under reflux. After refluxing for 1 hour, 3.6 mol equivalents of H$_2$O are added, and the mixture is stirred for a further 4 hours under reflux. The reaction solution is cooled, concentrated under vacuum, the residue taken up in hexane and the insoluble triphenylphosphine oxide filtered off. The filtrate is concentrated under vacuum, and the resultant amine is isolated as an oil, which is further reacted immediately. The amine is dissolved in 8 ml of DMF, together with 4-(tert.-butyloxycarbonyl)amidino-phenylacetic acid (733 mg, 2.64 mmol) and HOBT (4.89 mg, 3.19 mmol), and is reacted at room temperature with DCC (494 mg, 2.4 mmol). After 16 hours at room temperature, the suspension obtained is cooled to 0° C. and the precipitated dicyclohexylurea is filtered off. The filtrate is diluted with EtOAc and washed with saturated aqueous NaHCO$_3$ solution and saturated aqueous NaCl solution. After drying over Na$_2$SO$_4$, the product is concentrated under vacuum. The crude material obtained is chromatographed over silica gel (hexane/EtOAc, 30:70). The title compound is obtained as a white solid; MS: 727 (M+H)+.

I) (3S,5S)-6-[4-(tert.-butyloxycarbonyl)amidino-phenylacetylamino] -5-[((1,1-dimethylethyl)dimethylsilyl)oxy]-3-( 4-methoxyphenylpropionylamino)-hexanoic acid tert.-butylester The coupling product from stage H) of example 7 (1.23 g, 1.69 mmol) is dissolved in 8.5 ml of ethanol and hydrogenated over 10% Pd/C. After 2 hours at room temperature, the catalyst is removed by filtration, and the filtrate is concentrated under vacuum. The free amine obtained is dissolved in 5.6 ml of DMF, together with 4-methoxyphenylpropionic acid (335 mg, 1.86 mmol) and HOBT (345 mg, 2.25 mmol), and then mixed with DCC (349 mg, 1.69 mmol). After standing at room temperature for 63 hours, the suspension is cooled to 0° C., and worked up analogously to the process described in stage H) of example 7.

The crude product obtained is chromatographed over silica gel (hexane/EtOAc). The title compound is isolated as a white foam; MS: 755 (M+H)+.

J) (3S,5S)-6-(4-amidinophenylacetylamino)-5-hydroxy-3-(4-methoxyphenylpropionylamino)-hexanoic acid-δ-lactone The coupling product from stage I) of example 7 (639 mg, 0.846 mmol) is mixed with 0.21 ml of ethanedithiol, 0.21 ml of anisole and 4.23 ml of TFA/H$_2$O (95:5) at 0° C. After 3 hours at room temperature, the mixture is cooled again to 0° C., ether is added, and the precipitated solid is filtered off. The solid obtained is washed with ether and subsequently recrystallized. The trifluoroacetate of the title compound is obtained as a white crystalline substance. M.p. 216°–218° C.; [α]$_D$=+13.5° (c=0.48, MeOH), MS: 467 (M+H)+. The free compound is obtained from the trifluoroacetate in known manner.

EXAMPLE 8

(3S,5S)-6-(4-amidino-phenylacetylamino)-5-hydroxy-3-( 3-methyl-butyrylamino)-hexanoic acid-δ-lactone A) (3S,5S)-6-[4-(tert.-butyloxycarbonyl)amidino-phenylacetylamino]-5-[((1,1-dimethylethyl)-dimethylsilyl)oxy]-3-(3-methyl-butyrylamino)-hexanoic acid-tert.-butylester.

The coupling product from stage H) of example 7 (0.6 g, 0.82 mmol) is dissolved in 5 ml of ethanol and hydrogenated over 10% Pd/C. After 2 hours at room temperature, the catalyst is removed by filtration and the filtrate concentrated under vacuum. The free amine obtained is dissolved in 3 ml of DMF, together with isovaleric acid (110 μl, 0.9 mmol) and HOBT (172.5 mg, 1.13 mmol), and mixed with DCC (175 mg, 0.82 mmol). After 16 hours at room temperature, the reaction mixture is worked up analogously to the process described in stage I) of example 7. The crude product obtained is chromatographed over silica gel (hexane/EtOAc). The title compound is obtained as a white foam. MS: 677 (M+H)+.

B) (3S,5S)-6-(4-amidinophenylacetylamino)-5-hydroxy-3-( 3-methyl-butyrylamino)-hexanoic acid-δ-lactone The product from stage A) of example 8 (320 mg, 0.473 mmol) is treated with TFA analogously to stage J) of example 7, and the protecting group then removed. Following a precipitation reaction with ether and subsequent recrystallization, the trifluoroacetate of the title compound is obtained as a white crystallizate.

M.p.: 236.7°–237.7° C.; [α]$_D$=+15.0° (c=0.5 MeOH); MS: 389 (M+H)+.

The free compound is obtained from the trifluoroacetate in known manner.

EXAMPLE 9

(S)-3-N-[3-(p-methoxyphenyl)propionyl]amino-7-[N-(p-amidinobenzoyl)amino]heptanoic acid A) (S)-3-N-[3-(p-methoxyhenyl)propionyl]amino-7-N-Z-aminoheptanoic acid methylester 1.18 g of the trifluoroacetate obtained according to stage A of example 6 is reacted with 0.43 g of 3-p-methoxyphenylpropionic acid, 0.4 g of HOBT, 0.33 ml of triethylamine and 0.46 g of DCC and worked up, using the process described in stage B of example 6. The crude material obtained is recrystallized from ether, and the title compound is obtained in the form of white crystals; MS: 471 (M+H)+.

B) (S)-3-N-[3-(p-methoxyphenyl)propionyl]amino-7-N-Z-aminoheptanoic acid tert.-butylester Using the process according to stage B) of example 4, 0.7 g of the methylester obtained in stage A) of example 9 is hydrolyzed with 0.21 g of LiOH/H$_2$O, and the product of hydrolyzation is reacted with 0.82 g of tert.-butyl-2,2,2-trichloroacetimidate in the presence of 0.1 ml of boron trifluoroetherate, and worked up analogously. Following chromatography on silica gel (ethyl acetate/hexane 1:1), the title compound is obtained as a colourless oil; MS: 513 (M+H)+.

C) (S)-3-N-[3-(p-methoxyphenyl)propionyl]amino-7-[N-(p-amidinobenzoyl)amino]heptanoic acid 0.55 g of the compound obtained according to stage B) of example 9 is hydrogenated using the process described in stage C) of example 4, and the amine thus obtained is reacted with 0.28 g of N-Boc-p-amidinobenzoic acid, 0.18 g of HOBT, 0.15 ml of triethylamine and 0.22 g of DCC, using the process described in stage C) of example 4. The crude product obtained is purified by chromatography (silica gel, ethyl acetate) and deprotected with 5 ml of TFA/anisole (95/5). After precipitating with ether, the trifluoroacetate of the title compound is obtained in the form of a white powder. MS 469 (M+H)+.

The free compound is produced from the trifluoroacetate in known manner.

EXAMPLE 10

(3S,5S)-6-(4-amidinophenylacetylamino)-5-hydroxy-3-N-[2-(p-methoxyphenyl)ethanesulphonyl-amino]-hexanoic acid-δ-lactone.

A) (3S,5S)-6-[4-(tert.-butyloxycarbonyl)amidino-phenylacetylamino]-5-[((1,1-dimethylethyl) dimethylsilyl) oxy]-3-amino-hexanoic acid tert.-butylester.

1.09 g (1.50 mmol) of the title product of step H) of example 7 is mixed with 75.0 mg of PtO$_2$ in 7.50 ml of EtOH and hydrogenation is carried out by first heating under reflux for ¾ of an hour, after which 75 mg of Pd/C 10% is added and the mixture refluxed for a further ¾ of an hour. The catalyst is removed by filtration, 150 mg of Pd/C 10% is added to the filtrate which is refluxed for a further ½ an hour, after which a further 75 mg of Pd/C is added and refluxing continued for a further 1 hour. The catalyst is again removed by filtration, a further 150 mg of Pd/C 10% is added and refluxing continued for a further 1½ hours. The title product is then recovered by removal of the catalyst by filtration and evaporation to dryness. The crude product (890 mg) is approximately 100% pure, as judged by TLC, and is used for further synthesis without any additional purification.

B) (3S,5S)-6-[4-(tert.-butytoxycarbonyl)amidino-phenylacetylamino]5-hydroxy-3-N-[2-(p-methoxyphenyl)ethanesulphonylamino]-hexanoic acid tert.butylester.

890 mg (1.50 mmol) of the title compound of part A) of example 10 above and 99 μl of NMM (0.6 mol.equiv.) in 7.5 ml of THF is vigorously mixed with 193.5 mg (0.55 mol.equiv.) of 2-(p-methoxyphenyl)ethanesulphonyl chloride, under an atmosphere of nitrogen at room temperature for 2½ hours. A further 193.5 mg of the sulphonyl chloride and 99 μl of NMM are added and the mixture stirred as before at room temperature for 1 hour after which the mixture is left to stand for 18 hours at room temperature. The resultant reaction mixture is taken up as a suspension in EtOAc and extracted once with a 10% aqueous solution of acetic acid, once with aqueous $NaHCO_3$ solution and once with aqueous NaCl solution. The combined aqueous phases are further extracted once with EtOAc. The combined organic phases are then dried and evaporated to dryness using a Rotary evaporator. This yields 1.10 g of crude product, corresponding to a yield of about 92.70%. This crude product is purified on a 102.5 ml chromatographic column (silicagel 25–40 μm; eluent hexane/EtOAc 3:7; flowrate 10 ml/min; 10 ml fractions, Absorbance 0.02/200 my). Fractions 11 to 20 are pooled and the title product (257 mg) is recovered after evaporation of the solvent. $MA^+$791; $[MA-BOC]^+$691; $[MA-(BOC+C_4H_8)]^+$635.

C) (3S,5S)-6-[4-(tert-butyloxycarbonyl)amidino-phenylacetylamino]-5-hydroxy-3-N-[2-(p-methoxypheny 1)ethanesulphonylamino]-hexanoic acid-δ-lactone trifluoroacetic acid.

The title product (257 mg) of part B) of Example 10 is mixed with Anisol (100 μl) and ethanedithiol (100 μl) in 2 ml of 95% aqueous tifluoroaceticacid and left to stand at room temperature for 1⅓ hours. The resultant suspension is mixed vigorously whilst cooling in an ice bath with 20 ml of diethylether. The crystallised product is filtered off, washed with diethylether and dried under water pump vacuum at 40° C. The resultant crude product is dissolved in warm EtOH, the solution cooled and the product recrystallised to give the title product (158 mg) in purified form. The final product is analysed and has the following characterstics:

F : Ab 160° C.

$[\alpha]_D^{RT}=+12.8°$ c=0.25 in MeOH

221–896 Hf $MA^+$503

The free compound is produced from the trifluoroacetate in known manner.

EXAMPLE 11

Lithium (3S,5S)-6-(4-amidinophenylacteylamino)-5-hydroxy-3-( 4-methoxyphenylpropionylamino)-hexanoate.

153 mg (264 μmol) of the title compound of Example 7 dissolved in 528 μl of water is converted into the acetate form by anion exchange chromatography, using Bio-Rad ACr 1-X2 100-200 mesh anion exchange resin in acetate form. 2M acetic acid in water/acetonitrile (1:1) is used as eluent, the product containing fractions are evaporated, the residue dissolved in the minimum quantity of ethyl acetate and the product precipitated by addition of diethylether. The amorphous product residue is dissolved in water and mixed with 264 μl of 2N LiOH (2.00 mol. equ.) and left to stand at room temperature for 15 hours. The title product (87 mg, approximately 67% yield) is obtained from the resultant solution by evaporation and crystallisation from EtOH. On analysis the product is found to have the following characterstics:

Melting point=227°–230° C.

$[\alpha]_D^{RT}=11.6°$ (c=0.31 in $H_2O$)

$[M+Li]^+$ of the Lithium salt 497

—COOLi 491

$MH^+$

—COOH 485

The compounds of formula I are notable for their valuable therapeutic properties. In particular, the compounds of formula I possess the ability to inhibit the binding of fibrinogen to GP IIb/IIIa, and thus to prevent platelet aggregation.

The favourable properties of the compounds of formula I in inhibiting the binding of fibrinogen to isolated and immobilized GP IIb/IIIa and in inhibiting the ADP-induced aggregation of human blood platelets in the presence of fibrinogen are shown in the following tests:

a) Inhibition of binding of fibrinogen to isolated and immobilized GP IIb/IIIa: GP IIb/IIIa is isolated from membranes of human blood platelets by triton X-100 extraction and purified by chromatography on ion exchangers and by gel filtration. The receptor protein thus obtained is bonded to microtitre plates. The inhibition of the binding of biotin-labelled fibrinogen to the receptor in the presence of inhibitor is quantified.

b) Inhibition of the ADP-induced aggregation of human blood platelets in the presence of fibrinogen: Blood platelets are isolated from fresh whole-blood by centrifugation, and washed. The washed platelets are resuspended in the presence of PGI2 and apyrase and stimulated with ADP (10 mM) in the presence of fibrinogen. The ability of the platelets to aggregate in the presence or absence of inhibitors is quantified using an aggregometer.

The compounds of formula I effect an inhibition of the fibrinogen GP IIb/IIIa binding in a range of $IC_{50}$ (concentration of compounds of formula I which reduce the binding of fibrinogen to the receptor by 50%) of between 0.5 and 20 nM.

The inhibition of the ADP-induced platelet aggregation is brought about by compounds of formula I in a range of $IC_{50}$ (concentration of compounds of formula I at which 50% of platelet aggregation is inhibited) of between 20 and 100 nM.

The compounds of Examples 1 to 8 are tested to determine their $IC_{50}$ values in the inhibition of the fibrinogen GPIIb/IIIa binding (FB) and inhibition of the ADP-induced platelet aggregation (PA) test procedures described above. The results obtained are given below.

| | Product of Example: | | | | | | | |
|---|---|---|---|---|---|---|---|---|
| | 1 | 2 | 3 | 4 | 5 | 6 | 7 | 8 |
| FB: IC50 (nM) | 7.6 | 1.7 | 1.1 | 2.2 | 0.4 | 0.5 | 0.5 | 0.9 |
| PA: IC50 (nM) | 640 | 100 | 31 | 67 | 61 | 15 | 80 | 110 |

As a result of the activities shown in these tests, the compounds of formula I may be used for the prophylactic and acute treatment of thrombosis. Favourable results are obtained with doses of 0.1 to 20 mg/kg, preferably 0.1 to 3 mg/kg, per day for adults.

The compounds of formula I may similarly be employed in the form of salts, which are obtained by reacting them with pharmacologically acceptable acids such as acetic acid, trifluoroacetic acid, hydrochloric acid, etc.

Compounds of formula I, their solvates or salts may, e.g., in the form of a therapeutical composition containing one or more pseudopeptides of formula I or their salts, be administered enterally, e.g. orally (as tablets, capsules, etc.) or rectally or as a spray. Parenteral administration in the form of injection solutions and infusion solutions is also conceivable.

A is a group of the formula

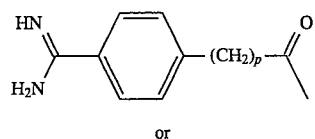

or

We claim:

1. A psuedopeptide of formula I or a pharmacalogically acceptable acid addition salt thereof

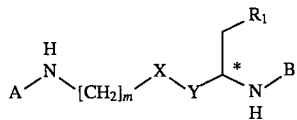

I wherein $R_1$ is —COOH, —COOM, —COO $(C_1$–$C_4)$alkyl;

M is an alkali or alkaline earth metal ion;

X is —$CH_2$—, —CO—, —C*HOH—, or —C*HO($C_1$–$C_4$)alkyl-, or

X and $R_1$ together are

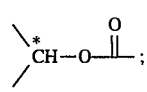

Y is —$(CH_2)_m$—;

and m is 1 or 2;

-continued

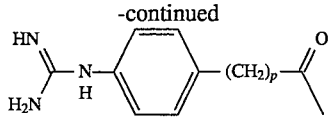

where p is 0, 1, or 2;

B is a group of the formula

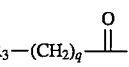

where q is 1 or 2 and $R_3$ is $(C_1$–$C_4)$alkyl, 1-adamantyl, trimethylsilyl, 1-naphthyl, phenyl, 3-indolyl, $(C_1$–$C_4)$alkoxyphenyl, or B is a group of the formula

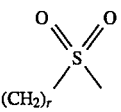

where r is 0, 1, or 2 and $R_4$ is $(C_1-C_4)$alkyl, phenyl, p-$(C_1-C_4)$alkoxyphenyl, 1-naphthyl, tolyl, mesyl, or trisyl.

2. A pseudopeptide according to claim 1 of formula

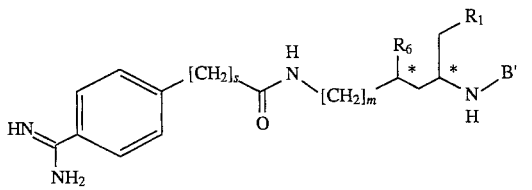   I' wherein $R_1$ and m are defined as in claim 1, s is 0 or 1, $R_6$=H, OH or O$(C_1-C_4)$alkyl.

$R_1$ and $R_6$ together form a —O—CO— group.

B' either denotes a group of formula

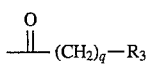

wherein $R_3$ and q are defined as in claim 1.

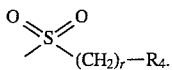

3. A pseudopeptide according to claims 2 of formula

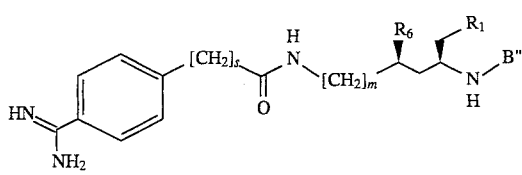   I'' wherein B'' denotes a group of formula

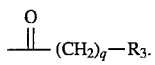

4. A pseudopeptide according to claim 1, selected from:

(S)-3-(N-tosylamino)-6-[N-(p-amidinophenylacetyl)amino]hexanoic acid (S)-3-[N-(3-methylbutyryl)amino]-6-[N-(p-amidinophenylacetyl)amino]hexanoic acid (S)-3-N-[3-(p-methoxyphenyl)propionyl]amino-6-[N-(p-amidinophenylacetyl)amino]hexanoic acid (S)-3-[N-(3-adamant-1-ylpropionyl)amino]-6-[N-(p-amidinophenylacetyl)amino]hexanoic acid (S)-3-[N-(3-methylbutyryl)amino]-7-[N-(p-amidinobenzoyl)amino]-heptanoic acid (3S,5S)-6-(4-amidinophenylacetylamino)-5-hydroxy-3-(4-methoxyphenyl-propionylamino)-hexanoic acid-δ-lactone (3S,5S)-6-(4-amidinophenylacetylamino)-5-hydroxy-3-(3-methylbutyryl-amino)-hexanoic acid-δ-lactone and (S)-3-N-[3-(p-methoxyphenylpropionyl]amino-7-[N-(p-amidinobenzoyl)amino]heptanoic acid (3S,5S)-amidinophenylacetylamino-5-hydroxy-3-N-[2-(p-methoxyphenyl) ethanesulphonylamino]-hexanoic acid-δ-lactone and Lithium (3S,5S)-6-(4-amidinophenylacetylamino)-5-hydroxy-3-( 4-methoxy-phenylpropionylamino)-hexanoate.

5. The pseudopeptide according to claim 1 which is (S)-3[N-(3-methylbutyryl)amino]-7-[N-(p-amidinobenzoyl)amino]-heptanoic acid.

6. A pharmacologically acceptable acid addition salt of a pseudopeptide according to claim 1.

7. A pharmaceutical composition comprising one or more pseudopeptides according to claim 1, together with a pharmaceutically acceptable carrier.

8. A method for the prophylactic or acute treatment of thrombosis in a subject in need of said treatment which comprises administering to said subject an effective amount of a pseudopeptide according to claim 1 or a pharmacologically acceptable acid addition salt thereof.

9. A pharmacologically acceptable salt of a pseudopeptide according to claim 2.

10. A pharmacologically acceptable salt of a pseudopeptide according to claim 3.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( v i ) ORIGINAL SOURCE:
        ( A ) ORGANISM: Homo sapiens ( x i ) SEQUENCE DESCRIPTION: SEQ ID NO:1:

His  His  Leu  Gly  Gly  Ala  Lys  Gln  Ala  Gly  Asp  Val
    1                    5                              10